United States Patent [19]
Mochizuki et al.

[11] Patent Number: 4,921,591
[45] Date of Patent: May 1, 1990

[54] ION SENSORS AND THEIR DIVIDED PARTS

[75] Inventors: Akihiko Mochizuki; Hideyo Iida, both of Tokyo, Japan

[73] Assignee: Taiyo Yuden Co., Ltd., Japan

[21] Appl. No.: 257,439

[22] Filed: Oct. 13, 1988

[30] Foreign Application Priority Data

| Oct. 13, 1987 | [JP] | Japan | 62-155625[U] |
| Jan. 25, 1988 | [JP] | Japan | 63-7103[U] |
| May 9, 1988 | [JP] | Japan | 63-110440 |
| Jul. 1, 1988 | [JP] | Japan | 63-162571 |

[51] Int. Cl.$^5$ ............................................. G01N 27/30
[52] U.S. Cl. ...................................... 204/412; 204/418; 357/25
[58] Field of Search ................... 357/25; 204/416, 418, 204/419, 420, 412

[56] References Cited

U.S. PATENT DOCUMENTS

| 4,020,830 | 5/1977 | Johnson et al. | 357/25 X |
| 4,437,969 | 3/1984 | Covington et al. | 204/403 |
| 4,508,613 | 4/1985 | Busta et al. | 204/418 |
| 4,735,702 | 4/1988 | Reinhoudt et al. | 204/416 |
| 4,778,769 | 10/1988 | Forrest et al. | 357/25 X |

FOREIGN PATENT DOCUMENTS 75250  7/1987  Japan.

Primary Examiner—G. L. Kaplan
Attorney, Agent, or Firm—King & Schickli

[57] ABSTRACT

An ion sensor includes an ion sensitive membrane formed from a vinyl polymer based compound containing a hydroxyl and/or carboxyl group. The membrane is provided on an extended gate electrode on a gate electrode of a field-effect type transistor. The ion sensor also includes a reference electrode arranged in opposition to the extended gate electrode. The extended gate electrode and reference electrode are formed on a substrate different from the substrate on which the field-effect type transistor is formed. A divided part for an ion sensor is also provided and includes the portions of the ion sensor discussed above except for the reference electrode. The divided part is used with a separate reference electrode.

17 Claims, 5 Drawing Sheets

ION SENSORS AND THEIR DIVIDED PARTS

TECHNICAL FIELD

The present invention relates to an ion sensor having an improved ion sensitive portion and its divided part.

BACKGROUND OF THE INVENTION

Ion sensors are designed to detect chemical substances with the use of a membrane having a cyclic compound called the ionophore or ion exchange resin fixed thereon. Such sensors detect chemical substances with excellent specificity. As one example, there is available an ion sensor for the measurement of the concentration of ions in a sample under examination, which uses an ion sensitive field-effect type transistor (hereinafter often abbreviated as ISFET).

The ISFET makes use of a conductivity change in the vicinity of a semiconductor surface, which occurs depending upon a field change on the interface of a solution and a sensitive membrane provided on the surface of that semiconductor.

Such ISFET's use of ion sensitive membrane formed on an insulating film on the gate of a field-effect type transistor (hereinafter often abbreviated as FET). There is also known an extended gate type ISFET of a structure where the ion sensitive membrane is isolated from the FET on the same semiconductor substrate.

As the ion sensitive membranes for these ISFET's, there are known hydrogen ion sensitive membranes formed of an inorganic material such as silicon nitride, aluminum oxide or indium oxide. Alternatively, use is made of an ion sensitive membrane formed of an organic material such as, for instance, a polyvinyl chloride membrane carrying thereon an active substance—called an ionophore—which selectively entrains ions. For instance, potassium and sodium ion sensitive membranes may be formed by using as the ionophores valinomycin and bis-(12-crown-4), respectively.

Just after preparation, an electrode coated with an ion sensitive membrane needs to be immersed and stored in an aqueous ion solution of the type to be examined. This is necessary to insure the stable operation of the ion sensitive membrane. Unfortunately, however, a problem may develop in that the polyvinyl chloride membrane does not adhere well to the surface of the electrode. This often causes the ion sensitive membrane to peel. Alternatively, vesicles or blisters may form along the interface between the membrane and the surface on which it is coated. Either of these problems serves to degrade the overall characteristics of the ion sensor. This is especially true of an ion sensor of the extended gate type ISFET structure where the gate electrode of the FET is extended to isolate the ion sensitive membrane from the FET portion through an extended connecting line. Where peeling or blisters occur, the floating capacity of the gate electrode is increased, resulting in decreases in its response rate.

In addition to the problems with the aforesaid ion sensitive membranes, there has been another problem with gate electrodes.

Namely, a metal such as silver or gold or an oxide such as $IrO_2$ or $SnO_2$ have heretobefore been used for an extended gate formed by extending the gate of the FET. With such an extended gate ISFET, it is virtually impossible to obtain a certain or higher current, e.g., on the order of micro-amperes due to the fact that a potential occurring on the ion sensitive membrane depends upon polarization. For that reason, there is a need of using a transducer having a high input impedance, while a floating capacity from the ion sensitive membrane to the gate electrode correlates with response rates. The latter point is of no substantial significance in the case of mounting the ion sensitive membrane on the gate insulating film but, in the case of the structure where the ion sensitive membrane is separated from the FET portion through a long connecting line, offers a problem that the floating capacity is too increased to decrease the response rates.

SUMMARY OF THE INVENTION

A first object of the present invention is to provide an ion sensor which includes an ion sensitive membrane showing an improved adhesiveness to electrodes, inter alia, an extended gate electrode and can be uniformly formed as well as a divided part including an extended gate having such an ion sensitive membrane.

A second object of the present invention is to provide an ion sensor which can obtain an increased current from potential occurring on an ion sensitive membrane and respond more rapidly even to a structure wherein a gate electrode portion having an ion sensitive membrane formed thereon is isolated from an FET portion through an extended connecting line as well as a divided part including such an extended gate electrode.

DETAILED DESCRIPTION OF THE INVENTION

For the sensitive membrane for the ISFET for which an organic material is used, it is preferred to use a vinyl polymer based compound containing a hydroxyl and/or carboxyl group so as to improve its adhesiveness and uniformity with respect to an electrode.

The vinyl polymer based compound containing a hydroxyl and/or carboxyl group may either contain both the hydroxyl and carboxyl (inclusive of an anhydrous carboxylic acid) groups, or be a mixture of the polymer compounds containing them separately. Further, use may be made of polyvinyl chloride, vinyl chloride/vinyl acetate copolymers and vinyl polymer based compounds obtained by the copolymerization of monomers other than hydroxyl and carboxyl groups. More specifically, use may be made of copolymers of vinyl chloride/vinyl acetate/vinyl alcohol, partly saponified products of vinyl chloride/vinyl acetate, copolymers obtained as a result of reaction with unsaturated carboxylic acids being reacted such as copolymers of vinyl chloride/vinyl acetate/maleic acid (or its anhydride) and so on. These vinyl polymer based compounds may further be copolymerized with other monomers.

The aforesaid vinyl polymer based compounds may also be used together with additives such as plasticizers, e.g., a plasticizer for vinyl resins.

In concrete embodiments, the vinyl polymer based compounds containing a hydroxyl and/carboxyl group are used as the component of ion sensitive membranes in the following manner.

Figure 1:
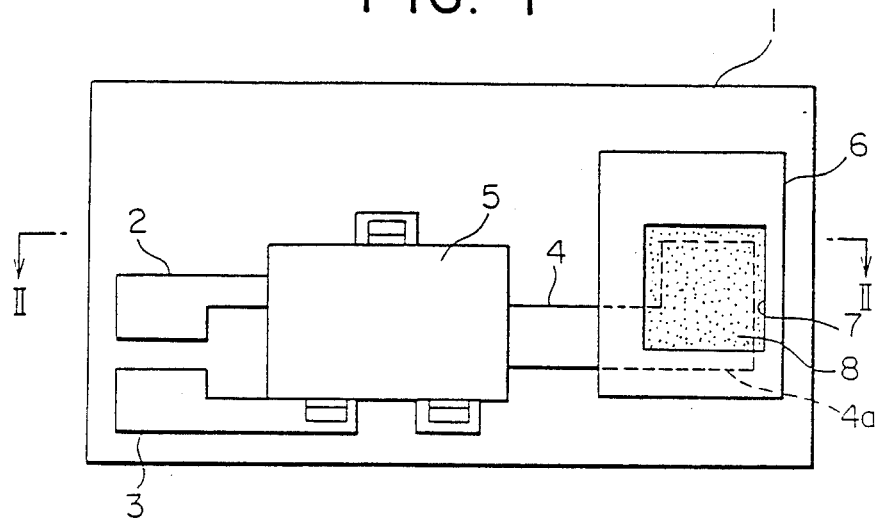
FIG. 1 is a plan view showing a main part of a first embodiment of the ion sensor according to the present invention.
Figure 2:
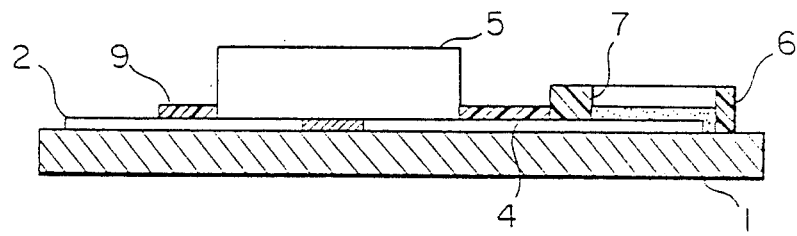
FIG. 2 is a sectional view taken along the line II—II of FIG. 1.

By soldering, an FET 5 is first connected and fixed to a source electrode 2, a drain electrode 3 and a gate electrode 4 formed on a glass substrate 1, as illustrated in FIGS. 1 and 2. The gate electrode 4 is then extended to form an extended gate electrode 4a on its extreme end, which is in turn provided there around with a bank body 6 comprising an insulating material such as an epoxy resin, thereby forming a window opening 7 through which a sample under examination is to be added dropwise. Finally, the extended gate electrode 4a facing to the window opening 7 is provided thereon with the following ion sensitive membranes 8.

(a) Prepared first was a solution of 0.2 g of polymer powders (#1000 GKT manufactured by Denka, Co., Ltd.) composed of vinyl-chloride/vinyl acetate/vinyl alcohol in a compositional proportion of 91:3:6 and having an average degree of polymerization of 420, 0.25 ml of dioctyl adipate and 2.5 mg of valinomycin in 3 ml of tetrahydrofuran. Ten (10) μl of this solution were added dropwise to the aforesaid electrode 4a for an extended gate and air-dried to form a potassium sensitive film as an ion sensitive membrane 8 having a thickness of about 80 μm.

(b) a potassium ion sensitive film was formed as an ion sensitive membrane 8 in a similar manner as stated in (a), except that polymer powders (#1000 CK manufactured by Denka, Co., Ltd.) composed of vinyl chloride/vinyl acetate/maleic acid in a compositional proportion of 86:13:1 and having an average degree of polymerization of 420 was used in place of the polymer powders used in (a).

Figure 3:
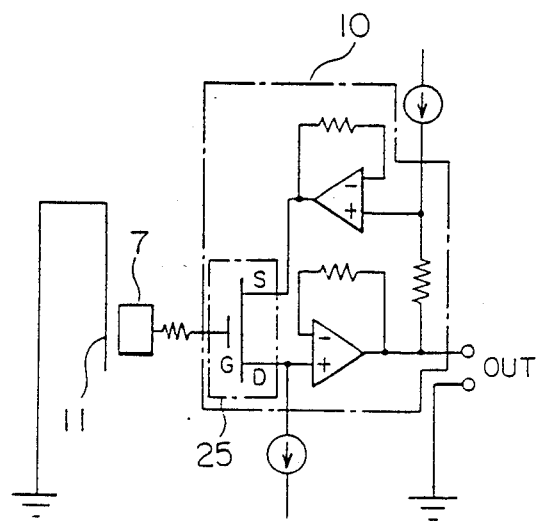
FIG. 3 is a measuring circuit diagram for the embodiments.

With each of the ion sensor parts provided thereon with these ion sensitive membranes and shown in FIG. 2, a potential on the surface of the potassium ion sensitive membrane was measured by a source follower circuit 10, shown in FIG. 3, using KCl-saturated Ag-/AgCl as a reference electrode 11, thereby determining the sensitivity of the potassium ion sensitive membrane at varied potassium ion concentrations of solutions.

The sensitivity of the ion sensitive membrane was measured just after its preparation as well as after its 7 and 14-day immersion and storage in 10 mM of KCl. The results are set forth in a table to be described later.

Further, whether or not vesicles or blisters were formed between the potassium ion sensitive membrane and the extended gate electrode 4a was visually observed after the lapse of 7 and 14 days. The results are set forth in the same table in which X and O denote the presence and absence of vesicles, respectively.

For the purpose of comparison, similar tests as mentioned above were carried out with the aforesaid gate electrode 4a on which an ion sensitive membrane, prepared in a similar manner as mentioned in (a) except that 0.2 g of a vinyl chloride resin manufactured by Aldrich, Co., Ltd. was used for the polymer powders used in (a), was formed in place of the aforesaid ion sensitivity membranes 8. The results are set forth in the following table.

| Ion Sensitive Membranes | Sensitivity (mV/pK) | | | Presence of Vesicles | | |
|---|---|---|---|---|---|---|
| | Date of Preparation | After 7 days | After 14 days | Date of Preparation | After 7 days | After 14 days |
| a | 52(100) | 52(100) | 52(100) | O | O | O |
| (b) | 49(100) | 49(100) | 49(100) | O | O | O |
| Comp. ex. | 52(100) | 49(100) | 40(77) | O | X | X |

It is noted that the racketed figures indicate the percent (%) with respect to the sensitivity of the ion sensitive membranes on the day on which they were prepared.

From the results set forth in the table, it is found that the ion sensitive membranes according to (a) and (b) adhere more closely to the extended gate electrodes, but the adhesion of the comparative membrane is weak (note presence of vesicles after 7 and 14 days).

It is appreciated that the composition of the ion sensitive membranes is variable by optimization.

While the foregoing has referred to the ion sensitive membranes, it is preferred that the electrode on which they are to be formed be either of a double-layer structure comprising two layers composed mainly of silver chloride and silver, respectively, or contain silver and silver chloride. If this is the case, it is then considered that the following reaction takes place between silver and silver chloride.

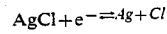

On the surface of the electrode, electrons (e−) enter or leave directly the silver electrode depending upon the concentration of Cl− ions. When a sensitive membrane for, e.g., potassium or sodium ions is used as the ion sensitive membrane, therefore, the concentration of Cl− ions fluctuates in correlation with the concentration of these K+ and Na−− ions. As a result, the aforesaid chemical reaction takes place to allow electrons to enter or leave the silver electrode. When a vinyl chloride film is used as the ion sensitive membrane in this case, moisture is allowed to be present on the surface of the AgCl electrode due to its slight water permeation, thus permitting the aforesaid chemical reaction to proceed easily.

The present invention will be now explained in more detail with reference to another embodiment.

Figure 4:
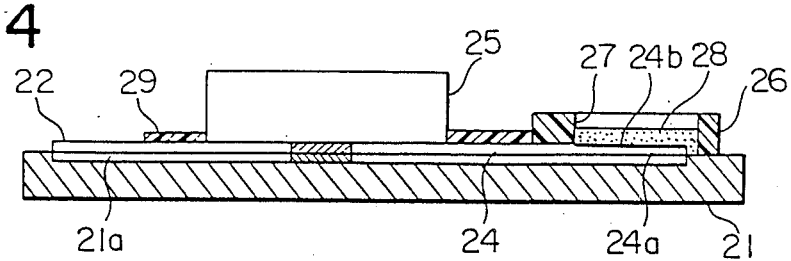
FIG. 4 is a sectional view corresponding to FIG. 2, showing a main part of a second embodiment of the ion sensor according to the present invention.

As illustrated in FIG. 4 corresponding to FIG. 2, a copper foil 21a is etched on a glass fiber reinforced epoxy resin substrate 21, and patterning for the formation of a circuit pattern is carried out to form a source electrode 22, a drain electrode 23 (not illustrated) and a gate electrode 24 on the substrate 21. This gate electrode is then extended to form an extended gate electrode 24a. Subsequently, the copper foil is silvered on the surface with a plating solution comprising silver and potassium cyanides. Further, the portion of the extended gate electrode 24a is treated at the surface in 0.1N HCl to form a silver chloride film 24b thereon.

Afterwards, a band body 26 comprising an insulating material such as an epoxy resin is provided to form a window opening 27 through which a sample under examination is to be added dropwise, and an FET 25 is soldered to the source electrode 22, drain electrode 23 and gate electrode 24.

Finally, a potassium ion sensitive film 28 was formed on the aforesaid extended gate 24a as the ion sensitive membrane in a similar manner as explained for the formation of the aforesaid ion sensitive membrane (a). It is noted that reference numeral 29 stands for an insulating film for an exposed portion of the gate electrode 24.

The thus obtained assembly may be combined with a separate reference electrode and used as a ion sensor. This is an example of the completely extended gate FET type structure.

Figure 5:
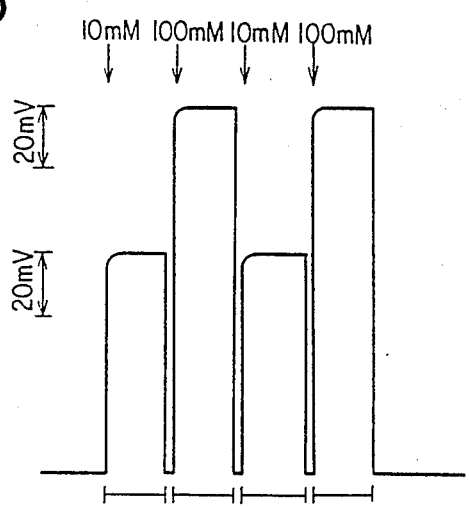
FIG. 5 is a diagram illustrating the results of measurement obtained with such an ion sensor.

With the thus obtained ion sensor part, a potential occurring on the surface of the ion sensitive membrane is measured by a source follower circuit 10, shown in FIG. 3, using KCl-saturated Ag/AgCl as a reference electrode 11, while varying alternately the potassium ion concentration of the solution between 20 mM and 200 mM, and was recorded on a recorder The results are shown in FIG. 5.

For the purpose of comparison, an ion sensor as shown in FIG. 4 was prepared in a similar manner as mentioned above, except that the portion of the aforesaid extended gate electrode 24a was not treated on the surface with silver chloride, and was used in combination with the aforesaid comparison electrode for similar measurement as already mentioned. The results are illustrated in FIG. 6.

Figure 6:
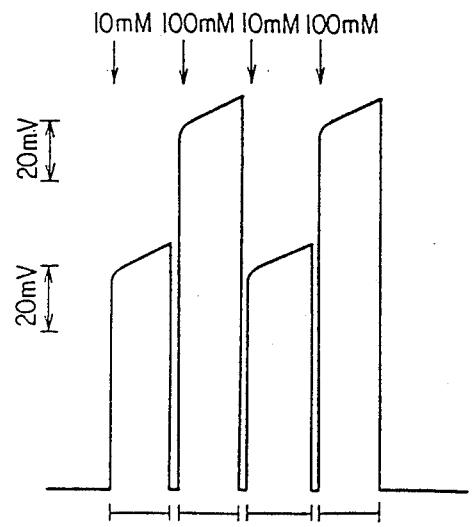
FIG. 6 is a diagram illustrating the results of measurement obtained with a conventional ion sensor for the purpose of comparison.

From FIGS. 5 and 6, it was found that the ion sensors having their extended gates treated with silver chloride according to the example of the present invention show no substantial drift (e.g., on the order of 1 mV/min. or lower) while they are immersed in the solutions having the respective potassium ion concentrations, whereas the ion sensor having its extended gate untreated with silver chloride according to the comparison example shows a drift of 4 mV/min. This indicates that the comparative ion sensor is poor in its response rate.

While the foregoing has referred to the double layer structure comprising two layers composed mainly of silver chloride and silver, respectively, a mixed layer of silver with silver chloride may be used. Such layers may be provided directly on a substrate, not on a copper foil. It is understood that the wording "composed mainly of silver chloride and silver" includes pure silver chloride and silver.

For the silver chloride treatment of an electrode of the double-layer structure comprising two layers composed mainly of silver chloride and silver, respectively, or an electrode containing silver chloride and silver, a silver electrode may be first prepared by plating, vapor deposition, sputtering or like other means and, then, treated with NaCl, FeCl$_3$ and so on.

While the foregoing embodiments have referred to the potassium ion sensors using valinomycin, other ions may be detected with similar effects by the replacement of ion sensitive substances. For instance, a sodium ion sensor may be prepared by using bis-12-crown-4 as an ion sensitive substance.

Figure 7:
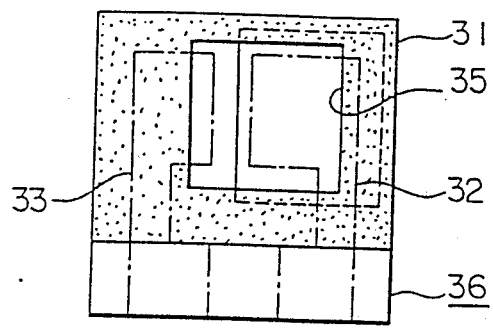
FIG. 7 is a plan view showing an ion sensing chip that is a divided part for an ion sensor used in a third embodiment of the present invention.

The ion sensitive membranes containing a vinyl polymer based compound having a hydroxy and/or carboxyl group and the electrodes of the double-layer structure comprising two layers composed mainly of silver chloride and silver or the electrodes containing silver chloride and silver according to the present invention may be used for the ion sensors of the structure where said membranes and/or said electrodes are formed independently or in combination on the gate insulating (preferably water-resistant) films of the FET's . They are also applicable to the ion sensors of the extended gate type FET structure where gates are extended and separated from the FET's main bodies and reference electrodes are incorporated on the same substrates. That is, as illustrated in FIG. 7, an extended gate electrode 32 and a reference electrode 33 are formed on a glass substrate 31, and a window opening 35, which is not covered with a resin 34 and through which a sample under examination is to be added dropwise, is formed. In this manner, an ion sensing chip 36 is prepared.

Figure 8:
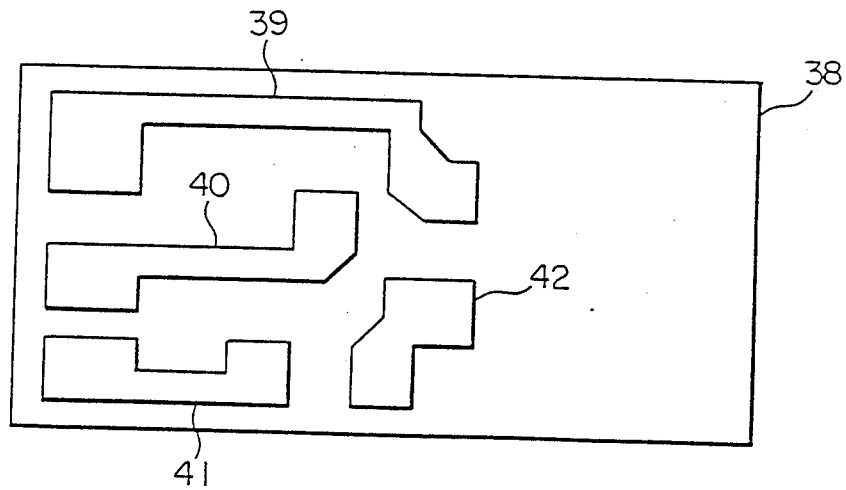
FIG. 8 is a plan view showing a circuit board.
Figure 9:
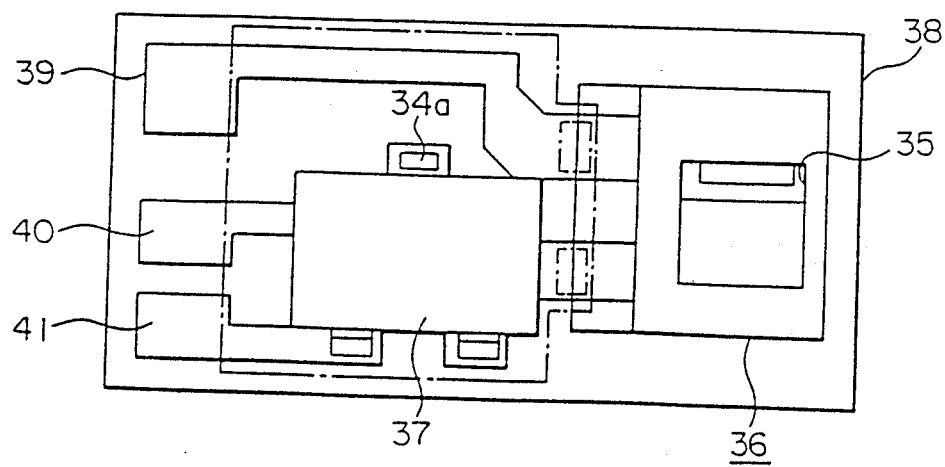
FIG. 9 is a plan view showing the circuit board into which the ion sensing chip is incorporated.
Figure 10:
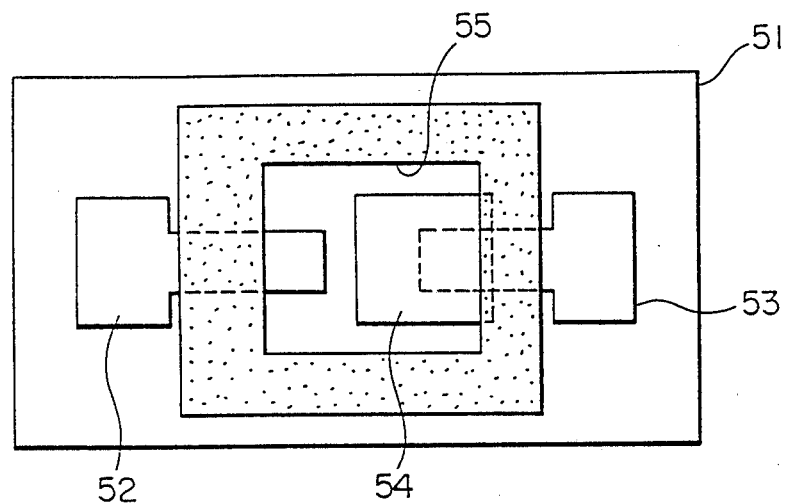
FIG. 10 is a plan view showing an ion sensing plate of a divided part for an ion sensor used in a fourth embodiment of the present invention.
Figure 11:
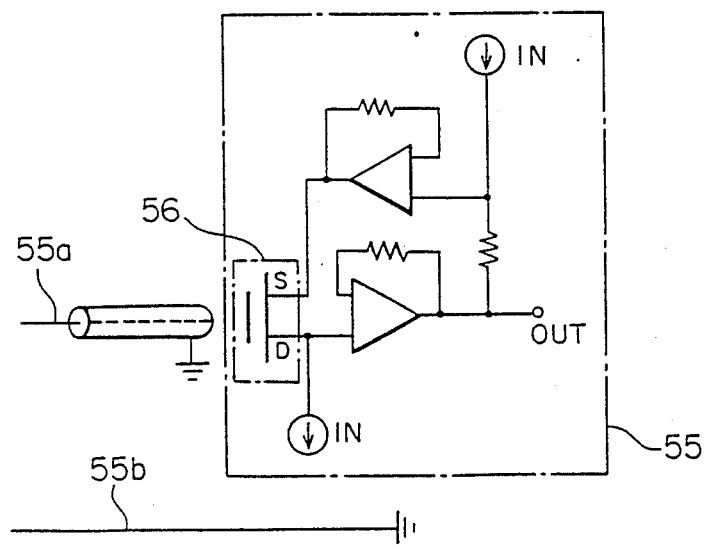
FIG. 11 is a measuring circuit diagram used with this ion sensing plate.

As illustrated in FIG. 8, on the other hand, reference, source, drain and gate electrode pieces 39, 40, 41 and 42 are formed on the substrate 38, and are connected to said ion sensing chip 36, as shown in FIG. 9. It is noted that reference numeral 37 is an FET. In a similar manner as mentioned above, the ion sensitive membranes and electrodes according to the present invention may further be applied to the ion sensitive membrane sensor plates which are used in combination with the FET's and in which only electrode portions to come in contact with samples under examination are separated, and the like. That is, as illustrated in FIG. 10, a reference electrode 52 and an extended gate electrode 53 are formed on a alumina substrate 51, and is then surrounded with a bank body 54 comprising a glass layer to form a window opening 55 through which a sample under examination is to be added dropwise. For use, the thus obtained assembly is connected, to leads 55a and 55 for the extended gate and reference electrodes of a circuit 55 shown in FIG. 11. It is noted that reference numeral 56 is an FET.

Figure 12:
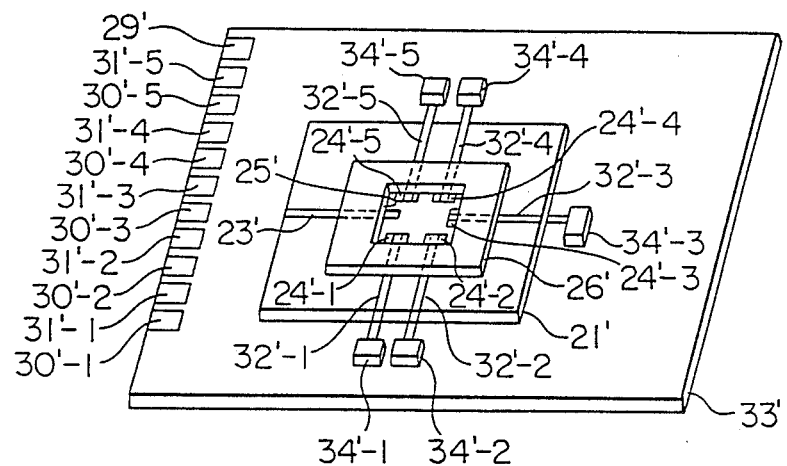
FIG. 12 is a perspective view of a fifth embodiment of the ion sensor according to the present invention.
Figure 13:
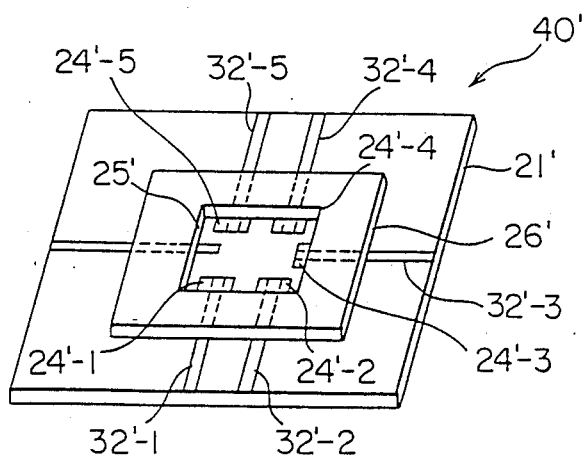
FIG. 13 is a divided part for that ion sensor.

According to the embodiments as described above, it is possible to measure- only one component contained in sample liquids. As illustrated in FIGS. 12 and 13, however, a similar circuit board 33 as illustrated in FIG. 8 may be radially provided thereon with five sets of lead pieces for reference, source, drain and gate electrodes similar to those shown in FIG. 8, and the lead pieces of each set may be connected together in a similar manner as shown in FIG. 9 and provided with FET's 34'-1, 34'-2, 34'-3, 34'-4 and 34'-5. Then, extended gate pieces (extended gate electrodes) 32'-1, 32'-2, 32'-3, 32'-4 and 32'-5 are provided on a glass substrate 21' with the one ends being centrically concentrated, as shown in FIG. 12, and are soldered to the lead pieces for gate electrodes of the FET's . These extended gate pieces are provided thereon with a bank body 26' of an epoxy resin to form a window opening 25' through which a sample is to be added dropwise. Further, the extended gate pieces are provided with ion sensitive membranes 24'-1, 24'-1, 24'-3, 24'-4 and 24'-5 carrying thereon such different ionophores as mentioned above.

It is noted that reference numeral 23' stands for a reference electrode having its end located in the window opening 25'. It is also noted that reference numerals 30'-2 to 30'-5 indicate source electrode terminals, 31'-1 to 31'-5 drain electrode terminals and 29' a reference electrode terminal. Connecting wires between the FET's and the reference electrode are coated on their surfaces with an insulating film, although not illustrated.

In the foregoing embodiment, the FET's and the window opening through which a sample is to be added dropwise are formed on the same substrate. However, the assembly of FIG. 13 may be used as a divided part 40', which is in turn connected to the associated parts, as illustrated in FIG. 12. In that case, the divided part 40' may be connected to the FET's and reference electrode terminal by insertion or like means.

Such a divided part may be replaced separately from the FET's.

In summary, according to the present invention, a vinyl polymer based compound having a hydroxyl and/or carboxyl group is incorporated into an ion sensitive membrane. The adhesiveness of the ion sensitive membrane to an extended gate electrode is thereby improved. Consequently, peeling and the occurrence of vesicles is avoided and the performance of the ion sensitive membrane is stabilized.

Further, since at least a surface layer portion of the extended gate electrode is comprised of a multi-layered structure consisting of two layers composed mainly of silver chloride and silver, respectively, or a layer containing silver chloride and silver, it is possible to provide an ion sensor which can obtain an increased current on the basis of a sensitivity value determined by the ion sensitive membrane formed on the extended gate, and reduce its floating capacity to increase its response rate.

We claim:

1. An ion sensor designed to determine an ion concentration of a sample liquid under examination with an ion sensitive membrane using a field-effect type transistor, said ion sensor comprising:
   a first substrate provided with a field-effect type transistor including a gate electrode;
   a second substrate including an extended gate electrode arranged in opposition to a reference electrode; said extended gate electrode being connected to said gate electrode; and
   said ion sensitive membrane being provided with said extended gate electrode and comprising a film containing a vinyl polymer based compound having a hydroxyl and/or carboxyl group.

2. An ion sensor as claimed in claim 1, wherein said reference electrode and said extended gate electrode on said second substrate form an ion sensing chip and further including a third substrate having wiring for connecting said ion sensing chip and said field-effect type transistor; and said third substrate and wiring effectively forming a circuit board onto which said field-effect type transistor and said ion sensing chip are mounted and connected.

3. An ion sensor as claimed in claim 2, further including a bank body for surrounding opposing portions of said reference electrode and said sensitive membrane formed on said second substrate, said bank body forming a window opening through which a sample liquid under examination is to be added dropwise.

4. An ion sensor as claimed in claim 2, wherein at least a surface-layer portion of said extended gate electrode is of a multi-layered structure comprising an upper layer composed mainly of silver chloride and a lower layer composed mainly of silver.

5. An ion sensor as claimed in claim 4, further including a bank body formed on said substrate for surrounding said extended gate electrode and said reference electrode, said bank body including a window opening through which a sample liquid under examination is to be added dropwise.

6. An ion sensor as claimed in claim 1, wherein at least a surface-layer portion of said extended gate electrode is of a multi-layered structure comprising an upper layer composed mainly of silver chloride and a lower layer composed mainly of silver.

7. An ion sensor as claimed in claim 1, wherein:
   a plurality of transistors including gate electrodes are formed on said first substrate;
   a plurality of extended gate electrodes to be connected with gate electrodes of said transistors and reference electrodes are provided on said second substrate;
   ion sensitive membranes being provided with said extended gate electrodes and comprising a film containing a vinyl polymer based compound having a hydroxyl and/or carboxyl group.

8. An ion sensor as claimed in claim 7 wherein at least each surface-layer portion of said extended gate electrodes is of a multi-layered structure comprising an upper layer composed mainly of silver chloride and a lower layer composed mainly of silver.

9. An ion sensor as claimed in claim 8, further including a bank body formed on said substrate for surrounding a plurality of said extended gate electrodes and said reference electrodes, said bank body including a window opening through which a sample liquid under examination is to be added dropwise.

10. A divided part for an ion sensor, comprising:
    a substrate;
    an extended gate on said substrate; and
    an ion sensitive membrane provided on said extended gate electrode wherein a vinyl polymer based compound containing a hydroxyl and/or carboxyl group is incorporated into said ion sensitive membrane.

11. A divided part for an ion sensor as claimed in claim 10, further including a reference electrode on said substrate.

12. divided part for an ion sensor as claimed in claim 11, further including a bank body formed on said substrate surrounding said extended gate and reference electrodes; said bank body forming a window opening through which a sample liquid under examination is to be added dropwise.

13. A divided part for an ion sensor, comprising:
    a substrate;
    an extended gate electrode on said substrate; and
    an ion sensitive membrane provided on said extended gate electrode having a surface layer portion of a multi-layered structure comprising an upper layer composed mainly of silver chloride and a lower layer composed mainly of silver and comprising a film containing a vinyl polymer base compound having a hydroxyl and/or carboxyl group.

14. A divided part for an ion sensor as claimed in claim 13, further including a reference electrode on said substrate.

15. A divided part for an ion sensor as claimed in claim 14, further including a bank body formed on said substrate surrounding said extended gate and reference electrodes; said bank body forming a window opening through which a sample liquid under examination is to be added dropwise.

16. A divided part for an ion sensor, comprising:
- a substrate;
- a plurality of extended gate electrodes and reference electrodes on said substrate; and
- ion sensitive membranes provided on said extended gate electrodes;
- each of said extended gate electrodes being of a multi-layered structure including an upper layer composed mainly of silver chloride and a lower layer composed mainly of silver; and wherein each of said ion sensitive membranes comprises a film containing a vinyl polymer based compound having a hydroxyl and/or carboxyl group.

17. A divided part for an ion sensor as claimed in claim 16, further including a bank body formed on said substrate surrounding a plurality of said extended gate electrodes and said reference electrodes;
said bank body including a window opening through which a sample liquid under examination is to be added dropwise.

* * * * *